United States Patent
Fay et al.

(10) Patent No.: US 8,840,751 B2
(45) Date of Patent: *Sep. 23, 2014

(54) BONDING COMPOSITIONS

(75) Inventors: Nigel Fay, Kildare (IE); Darren Nolan, Dublin (IE); Eimear M. Fleming, Dublin (IE); Brendan J. Kneafsey, Dublin (IE); Rainer K. Wefringhaus, Hilden (DE)

(73) Assignee: Henkel IP & Holding GmbH, Duesseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/412,745

(22) Filed: Mar. 6, 2012

(65) Prior Publication Data

US 2012/0164904 A1 Jun. 28, 2012

Related U.S. Application Data

(63) Continuation of application No. PCT/EP2010/062756, filed on Aug. 31, 2010.

(60) Provisional application No. 61/241,690, filed on Sep. 11, 2009.

(51) Int. Cl.
| | | |
|---|---|---|
| *C09J 7/02* | (2006.01) | |
| *B32B 9/04* | (2006.01) | |
| *C07F 7/10* | (2006.01) | |
| *D06M 15/643* | (2006.01) | |
| *C08G 77/04* | (2006.01) | |
| *C09J 5/06* | (2006.01) | |
| *C07F 7/18* | (2006.01) | |
| *C08K 5/33* | (2006.01) | |
| *C08K 5/544* | (2006.01) | |
| *C08K 3/34* | (2006.01) | |
| *C08K 5/5419* | (2006.01) | |
| *C08K 5/32* | (2006.01) | |
| *C08K 3/22* | (2006.01) | |

(52) U.S. Cl.
CPC .......... *C08G 77/045* (2013.01); *G09J 2421/006* (2013.01); *C08K 5/33* (2013.01); *C08K 5/544* (2013.01); *C09J 5/06* (2013.01); *C08K 3/34* (2013.01); *C09J 2400/143* (2013.01); *C07F 7/1836* (2013.01); *C09J 2407/006* (2013.01); *C08K 5/5419* (2013.01); *C08K 5/32* (2013.01); *C08K 3/22* (2013.01)
USPC .......................... 156/325; 156/326; 156/329; 428/446; 428/448; 428/450; 556/419; 556/421; 106/287.11

(58) Field of Classification Search
None
See application file for complete search history.

(56) References Cited

U.S. PATENT DOCUMENTS

| | | | |
|---|---|---|---|
| 3,542,639 A | | 11/1970 | Manino |
| 4,308,071 A | * | 12/1981 | Gervase ............................ 528/10 |
| 5,429,772 A | * | 7/1995 | Castellucci et al. ............ 252/514 |
| 5,834,100 A | * | 11/1998 | Marks et al. ................... 428/209 |
| 8,128,996 B2 | * | 3/2012 | Davies et al. ............... 427/372.2 |
| 8,153,268 B1 | * | 4/2012 | Fay et al. ....................... 428/448 |
| 2004/0259992 A1 | | 12/2004 | Gobel |
| 2008/0114111 A1 | | 5/2008 | Hoy et al. |

FOREIGN PATENT DOCUMENTS

| | | |
|---|---|---|
| EP | 1167455 | 1/2002 |
| GB | 1526953 | 10/1978 |
| WO | 2009118255 | 10/2009 |
| WO | 2010106029 | 9/2010 |
| WO | 2010106030 | 9/2010 |

OTHER PUBLICATIONS

Stegmaier, P., Alonso, J., Campo, A., Photoresponsive Surfaces with Two Independent Wavelength-Selective Functional Levels, Sep. 26, 2008, American Chemical Society, vol. 24, pp. 11872-11879.*
International Search Report issued in connection with International Patent Application No. PCT/EP2010/062756 mailed on Feb. 1, 2011.
Vanderbilt, "Bonding of fibrous glass to elastomers", Indus. Eng. Chem.—Product Research Development: Industrial and Engineering Chemistry—Product Research and Development, vol. 4, No. 1, pp. 18-22 (1965).

* cited by examiner

*Primary Examiner* — Michael H Wilson
*Assistant Examiner* — Christine Rea
(74) *Attorney, Agent, or Firm* — Steven C. Bauman

(57) ABSTRACT

Methods for bonding polymeric substrates to hydroxylated surfaces such as glass are disclosed. The polymeric substrates may be elastomeric substrates such as a natural or synthetic rubber. The method may comprise applying a compound comprising at least one alkoxy silane moiety and at least one moiety selected from a nitrosoaromatic or a nitrosoaromatic precursor to one of the substrates. The nitrosoaromatic moiety may be a nitrosobenzene. The nitrosoaromatic precursor may be a nitrosobenzene precursor, such as at least one of a quinone dioxime or a quinone oxime. Novel primers and compounds suitable for use in the bonding process are also disclosed.

10 Claims, No Drawings

BONDING COMPOSITIONS

BACKGROUND

1. Field

Curable compositions such as adhesive compositions for bonding polymeric substrates to hydroxylated surfaces are disclosed. In particular, adhesive compositions suitable for use in polymer-to-glass, for example elastomer-to-glass such as rubber-to-glass, bonding applications are provided. One aspect of the invention provides novel compounds suitable for use in adhesive compositions suitable for rubber to glass bonding applications.

2. Brief Description of Related Technology

Reinforced composite materials play a critical role in the manufacture of high-performance products that need to be lightweight, yet strong enough to take harsh loading and operating conditions. Popular reinforcing materials included wood, glass, metals, quartz and carbon fibres. Composites reinforced with such materials may find utility in the manufacture of a number of structural materials such as aerospace components and racing car bodies.

Per unit weight glass represents one of the strongest structural materials around, and, for example, is stronger than steel on a weight per weight basis. Furthermore, glass exhibits improved stress and strain resistance compared to many other common reinforcement media. For example, glass cord may be utilised to exploit the unique properties of glass fibres to impart strength and dimensional stability to polymeric products.

Glass fibre reinforced composite materials consist of high strength glass fibres embedded in a matrix. For example, Glass Fibre Reinforced Concrete comprises glass fibres embedded in cement-based matrix and may find utility in buildings and other structural edifices. Similarly, Glass Reinforced Plastic comprises glass fibres embedded in a plastic material. Glass Reinforced Plastics are immensely versatile materials which combine to provide lightweight materials with high strength performance. Glass reinforced plastics find utility in a number of different areas from structural engineering to telecommunications.

Elastomer to glass bonding provides an attractive means by which the structural strength of glass can be combined with the elastomeric properties of the elastomer/rubber. Reinforcing fibres such as glass fibres have been used as a reinforcing material for rubber articles such as in rubber belts, tyres and hoses. In particular, glass fibres have been employed to reinforce automotive timing belts, where there is a need for synchronous transfer of power from crankshaft to overhead camshaft without loss of inertia.

In general, rubber articles are repeatedly subjected to a flexing stress resulting in flex fatigue. This can lead to reduced performance, a peel-off between the reinforcing fibre and a rubber matrix and a wearing of the reinforcing fibre. Accordingly, adhesives for rubber to glass bonding should be capable of enduring such stresses.

Traditionally, such glass cord composites are manufactured by coating individual filaments of glass yarn with specialised coatings, such as resorcinol formaldehyde latex (RFL) formulations. Conventional rubber to metal bonding products are then employed to bond the RFL latex to the rubber via a vulcanisation step.

Traditional rubber to metal bonding technology, incorporates a two-step system, where in a first step a primer is applied and thereafter in a second step an adhesive is applied. The primer ordinarily consists of solutions or suspensions of chlorinated rubber and phenolic resins containing reactive groups, and also pigments such as titanium dioxide, zinc oxide, carbon black, etc. The primer is generally applied as a thin layer onto a treated (cleaned) surface of a metallic component such as treated steel component for example a component that has been grit blasted or chemically treated. The adhesive ordinarily consists of a large range of rubber materials and cross-linkers. These include, but are not restricted to, chlorinated and bromochlorinated rubbers, aromatic nitrosobenzene compounds and bismaleimide as cross-linkers, xylene, perchloroethylene and ethylbenzene as solvents, and also some lead or zinc salts. The adhesive layer is generally the link between the primed metal and the rubber.

Generally, it is desirable that bonding to the target substrate is achieved during a vulcanisation step like compression moulding, transfer moulding, injection moulding and autoclave heating, for example with steam or hot air. For example, semi-solid rubber can be injected into a mould. The semi-solid rubber is then cross-linked into a fully cured rubber and the bond with the substrate is formed at the same time.

Certain requirements of the curing system are desirable. This includes, ease of processing, stability (for example avoiding sedimentation), ease of application, fast drying (to allow handling without fouling), good wetting properties, and good curing strengths. Curing should be achieved independently of the type of elastomer (rubber) employed and also independently of the type of substrate. It will be appreciated that some rubbers are blended materials and accordingly it is desirable that good curing is achieved with such blended materials. Suitably consistent curing is achieved under various process parameters. Durability is also desirable.

Notwithstanding the state of the art it would be desirable to provide compounds and compositions to bond polymeric substrates (for example elastomers) to hydroxylated substrates such as glass.

SUMMARY

The present invention provides for a method of bonding polymers to hydroxylated surfaces. Polymer to glass bonding, such as elastomer to glass bonding, for example rubber to glass bonding may be beneficial in applications wherein the properties of metals, such as high molecular weights, susceptibility to corrosion, durability and cost detracts from their suitability in particular applications.

In a first aspect, the present invention provides for a method for bonding a polymer to a hydroxylated surface, the method comprising:

applying a compound comprising;
a) at least one alkoxy silane moiety; and
b) at least one moiety selected from an aromatic nitroso or an aromatic nitroso precursor and combinations thereof, to at least one of the surface or the polymer and bringing the surface and polymer together. The compound may be applied to the hydroxylated surface.

The method may further comprise the step of heating subsequent to bringing the substrates together. Advantageously, heating may increase the rate of bond formation. Heating may improve bond strength.

As used herein the term hydroxylated surface refers to any substrate with a surface comprising an atom bonded to a hydroxy group. Suitable non-limiting examples include a hydrous metal oxide, glass substrates comprising surface Si—OH bonds or clay substrates comprising surface Al—OH bonds. Suitable hydroxylated surfaces include those of silicates, aluminates, germanates and combinations thereof. The hydroxylated surface may be a silicate, an aluminate or combinations thereof. As used herein, the term silicate refers to substrates comprising Si—OH bonds. The term aluminate refers to substrates having Al—OH bonds and the term germinate refers to substrates having Ge—OH bonds.

For example, the hydroxylated surface may be one of glass such as glass fibres, quartz, clays, talcs, zeolites, porcelains, ceramics, silicon substrates such as silicon wafers and combinations thereof.

The polymer may comprise alkene and/or allylic functionality within the polymer chain. For example, diene and/or allylic functionality may be present within the polymer chain. Suitably, the polymer may comprise allylic functionality. Suitable polymers may include elastomers. Suitable elastomers may comprise natural or synthetic rubbers. The synthetic rubber may be a nitrile butadiene rubber. The synthetic rubber may be a hydrogenated nitrile butadiene rubber (HNBR). The polymer may be a $C_2$-$C_{1,000,000}$ polymer, such as a $C_2$-$C_{10,000}$ polymer.

The at least one moiety selected from an aromatic nitroso or an aromatic nitroso precursor may be a nitrosobenzene or a nitrosobenzene precursor and combinations thereof.

The method of the present invention may additionally comprise the step of cleaning, for example abrasively cleaning, such as blasting, for example grit-blasting the hydroxylated surface prior to application of the compound thereto. Cleaning may reveal nascent hydroxyl groups on the surface, thereby greatly enhancing the ability of the adhesive to bond the hydroxylated surface and the polymer, such as an elastomer, for example a rubber together.

Within the context of this specification the term aromatic nitroso moiety refers to an aromatic moiety having at least one nitroso group. Similarly, the term aromatic nitroso precursor moiety refers to any compound that is capable of being transformed into an aromatic nitroso moiety with at least one nitroso group. The term aromatic comprises both fused and non-fused aromatic rings.

For example, a non-limiting selection of fused and non-fused aromatic nitroso moieties embraced by the present invention are detailed below:

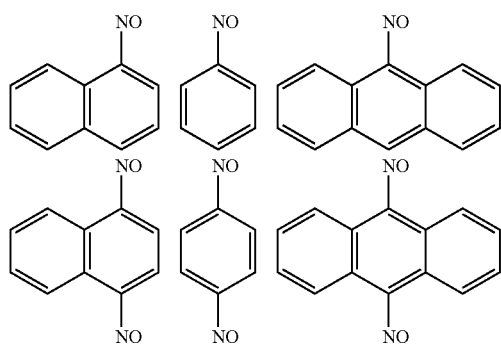

As will be appreciated by a person skilled in the art, the nitroso structures disclosed above may optionally be substituted one or more times, for example with at least one of $C_1$-$C_{20}$ alkyl, $C_1$-$C_{20}$ cycloalkyl, $C_1$-$C_{20}$ alkoxy, $C_6$-$C_{20}$ aralkyl, $C_6$-$C_{20}$ alkaryl, $C_6$-$C_{20}$ arylamine, $C_6$-$C_{20}$ arylnitroso, cyano, amino, hydroxy, halogen and combinations thereof. Such substitutions are possible provided there is no interference with effective bonding or curing of a composition comprising the compound.

The compounds used in the method of the present invention may assist in the formation of polymer to glass bonds, such as elastomer to glass bonds, for example rubber to glass bonds. They can be easily applied at the interface between the rubber and the glass and assist in developing strong and durable bonds during the curing process.

Within the method of the present invention, and in contrast to conventional systems, the compound utilised in the method of the present invention can be applied (as part of an adhesive composition) to unvulcanised rubber (as distinct from a non-elastomeric substrate) prior to vulcanisation and bond formation, and upon subsequent vulcanization a bond results. This means that the compound/adhesive system may be applied to a rubber or a glass substrate. The compound may be applied to a glass substrate.

The aromatic nitroso precursor moiety may comprise an oxime, a dioxime and combinations thereof. For example, the aromatic nitroso precursor moiety may be the mono- or dioxime of a compound selected from the group consisting of:

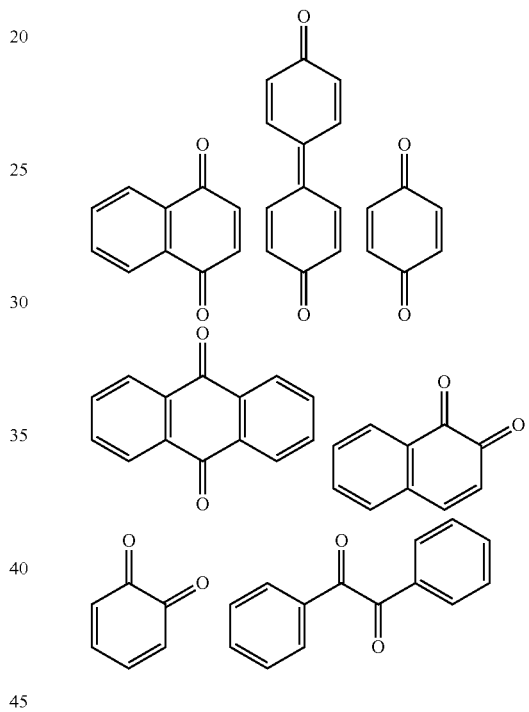

As will be appreciated by a person skilled in the art, the diketone structures disclosed above may optionally be substituted one or more times, for example with at least one of $C_1$-$C_{20}$ alkyl, $C_1$-$C_{20}$ cycloalkyl, $C_1$-$C_{20}$ alkoxy, $C_6$-$C_{20}$ aralkyl, $C_6$-$C_{20}$ alkaryl, $C_6$-$C_{20}$ arylamine, $C_6$-$C_{20}$ arylnitroso, cyano, amino, hydroxy, halogen and combinations thereof. Such substitutions are possible provided there is no interference with effective bonding or curing of a composition comprising the precursor compound, for example, provided there is no interference with the generation of an aromatic nitroso compound in-situ.

The aromatic nitroso moiety of the compound utilised in the method of the present invention may comprise a nitrosobenzene moiety. The nitrosobenzene moiety may be a mononitrosobenzene, a dinitrosobenzene, or combinations thereof. Similarly, the aromatic nitroso precursor moiety of the composition of the present invention may comprise a nitrosobenzene moiety precursor. The nitrosobenzene precursor may be a mononitrosobenzene precursor, a dinitrosobenzene precursor, or combinations thereof. It will be appreciated that the nitrosobenzene precursor may form one of a nitrosobenzene structure, a dinitrosobenzene structure or apara-nitrosophenol structure in-situ. The nitrosobenzene precursor may be at least one of a quinone dioxime or a quinone oxime. It has been found that such structures assist in the formation of desirable bonds.

As will be appreciated by a person skilled in the art, references to nitrosobenzene and nitrosobenzene precursor moieties include nitrosobenzene and nitrosobenzene precursor moieties that may optionally be substituted one or more times with at least one of $C_1$-$C_{20}$ alkyl, $C_3$-$C_{20}$ cycloalkyl, $C_1$-$C_{20}$ alkoxy, $C_6$-$C_{20}$ aralkyl, $C_6$-$C_{20}$ alkaryl, $C_6$-$C_{20}$ arylamine, $C_6$-$C_{20}$ arylnitroso, cyano, amino, hydroxy, halogen and combinations thereof. Such substitutions are possible provided there is no interference with effective bonding or curing of a composition comprising these compounds. For example, provided there is no interference with the generation of a nitrosobenzene moiety in-situ.

The silane moiety of the compound utilised in the method of the present invention may be of the structure:

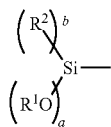

where 'a' can be 1-3 and 'b' can be 0-2, wherein a+b=3 and at least one alkoxy group is present;
$R^1$ can be selected from H, $C_1$-$C_{24}$ alkyl, $C_3$-$C_{24}$ acyl, preferably from $C_1$-$C_4$ alkyl;
wherein when a≥1 at least one $R^1$ is not hydrogen; and
$R^2$ can be selected from $C_1$-$C_{24}$ alkyl and $C_3$-$C_{24}$ acyl, preferably from $C_1$-$C_4$ alkyl.

In one embodiment, a is 3 and $R^1$ is $C_1$-$C_{24}$ alkyl. $R^1$ may be $C_1$-$C_4$ alkyl and a may be 3.

The compounds may be reaction products derived from an isocyanate or isothiocyanate and an active hydrogen compound, such as —$NH_x$ (where x=1 or 2), —SH, or —OH. In this manner the so-described compounds should contain at least one linkage described by:

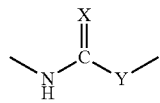

where X can be S or O, and Y includes —$NH_x$ (where x=1 or 2), —S, or —O.

The general structure for these compounds is shown below:

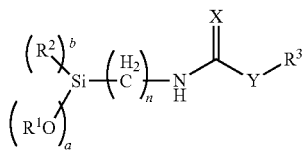

where 'a' can be 1-3 and 'b' can be 0-2; wherein a+b=3 and at least one alkoxy group is present;
$R^1$ can be selected from H, $C_1$-$C_{24}$ alkyl or $C_3$-$C_{24}$ acyl, preferably from $C_1$-$C_4$ alkyl, and where when a≥1 at least one $R^1$ is not hydrogen; and
$R^2$ can be selected from $C_1$-$C_{24}$ alkyl and $C_3$-$C_{24}$ acyl, preferably from $C_1$-$C_4$ alkyl; n can be 1-10;

X can be O or S;
Y can be —O, —S, or —$NH_x$ (where x=1 or 2); and
$R^3$ may be a moiety comprising nitrosoaromatic, or a nitrosoaromatic precursor as defined herein.

$R^3$ may be a moiety comprising nitrosobenzene, quinone dioxime or quinone oxime.

$R^1$ may be selected from $C_1$-$C_{24}$ alkyl or $C_3$-$C_{24}$ acyl. $R^1$ may be selected from $C_1$-$C_{24}$ alkyl or $C_3$-$C_{24}$ acyl and 'a' may be 3. X may be O. Y may be O or —$NH_x$ (where x=1). Y may be O. X and Y may be O. $R^1$ may be selected from $C_1$-$C_4$ alkyl, X may be O and 'a' is 3. $R^1$ may be selected from $C_1$-$C_4$ alkyl, X may be O, Y may be O and 'a' may be 3. $R^1$ may be selected from $C_1$-$C_4$ alkyl, X may be O, Y may be $NH_x$ (where x=1) and 'a' may be 3. $R^1$ may be selected from $C_1$-$C_4$ alkyl, X may be O, Y may be O, 'a' may be 3 and $R^3$ may be a moiety comprising nitrosobenzene.

Structures for $R^3$, showing the linkage through 'Y', can include:

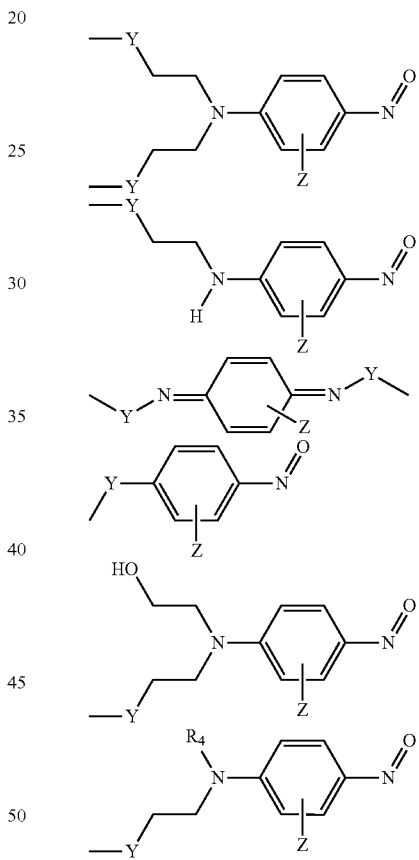

where $R_4$ can be $C_1$ to $C_{10}$; and
Z indicates that the rings of the above structures can optionally be mono-, di-, tri- or tetrasubstituted with the group consisting of $C_1$-$C_{20}$ alkyl, $C_3$-$C_{20}$ cycloalkyl, $C_1$-$C_{20}$ alkoxy, $C_6$-$C_{20}$ aralkyl, $C_6$-$C_{20}$ alkaryl, $C_5$-$C_{20}$ arylamine, $C_5$-$C_{20}$ arylnitroso, amino, hydroxy, halogen and combinations thereof, and further where the substituents can either be the same or different on each carbon atom of the ring. Such substitutions may be possible provided there is no interference with effective bonding or curing of the compositions. For example, provided there is no interference with the generation of a nitrosobenzene compound in-situ.

In a related embodiment, the compound utilised in the method of the present invention may have the general structure:

$$\left(R^2\right)_b \underset{\left(R^1O\right)_a}{Si} - \left(CH_2\right)_n - \underset{H}{N} - \overset{X}{\underset{\parallel}{C}} - Y - N = \left\langle = \right\rangle = N - Y - \overset{X}{\underset{\parallel}{C}} - \underset{H}{N} - \left(CH_2\right)_n - \underset{c}{Si} \left(R^2\right)_d \left(OR^1\right)_c$$

where n can be 1-10;
'a' can be 1-3 and 'b' can be 0-2; wherein a+b=3 and at least one alkoxy group is present;
c can be 'a' or 1 to 3; d can be 'b' or 1 to 3;
$R^1$ can be selected from H, $C_1$-$C_{24}$ alkyl or $C_3$-$C_{24}$ acyl, preferably from $C_1$-$C_4$ alkyl and where when a≥1 at least one $R^1$ is not hydrogen;
$R^2$ can be selected from $C_1$-$C_{24}$ alkyl and $C_3$-$C_{24}$ acyl, preferably from $C_1$-$C_4$ alkyl;
X can be O or S; and
Y can be —O—, —S—, or —$NH_x$ (where x=1 or 2).

$R^1$ may be selected from $C_1$-$C_{24}$ alkyl or $C_3$-$C_{24}$ acyl. $R^1$ may be selected from $C_1$-$C_{24}$ alkyl or $C_3$-$C_{24}$ acyl and 'a' may be 3. X may be O. Y may be O or —$NH_x$ (where x=1). Y may be O. X and Y may be O. $R^1$ may be selected from $C_1$-$C_4$ alkyl, X may be O and 'a' is 3. $R^1$ may be selected from $C_1$-$C_4$ alkyl, X may be O, Y may be O and 'a' may be 3. $R^1$ may be selected from $C_1$-$C_4$ alkyl, X may be O, Y may be —$NH_x$ (where x=1) and 'a' may be 3. $R^1$ may be selected from $C_1$-$C_4$ alkyl, X may be O, Y may be O, n may be 3 and 'a' may be 3.

In a further embodiment, the compound utilised in the method of the present invention may be an oligomeric or co-oligomeric compound of the general structure:

$$\left[\begin{array}{c} R^2 \\ | \\ \left(R^1O - \underset{|}{Si} - \left(CH_2\right)_p - R^4\right)_q \\ O \\ | \\ R^1O - \underset{|}{Si} - \left(CH_2\right)_n - \underset{H}{N} - \overset{X}{\underset{\parallel}{C}} - Y - R^3 \\ | \\ R^2 \end{array}\right]_m$$

where m can be 1-100; n can be 1-10; p can be 1-10; q can be 0-50; and if q=0, m≥2;
$R^1$ can be selected from H, $C_1$-$C_{24}$ alkyl or $C_3$-$C_{24}$ acyl, and preferably from $C_1$-$C_4$ alkyl;
$R^2$ can be selected from $OR^1$, $C_1$-$C_{24}$ alkyl or $C_3$-$C_{24}$ acyl, and where when $R^2$=$OR^1$ at least one $R^1$ is not hydrogen;
$R^4$ can be selected from acrylate, aldehyde, amino, anhydride, azide, maleimide, carboxylate, sulphonate, epoxide, ester functional, halogens, hydroxyl, isocyanate or blocked isocyanate, sulfur functional, vinyl and olefin functional, or polymeric structures;
X can be O or S;
Y can be —O—, —S—, or —$NH_x$ (where x=1 or 2); and
$R^3$ may be a moiety comprising nitrosoaromatic, or a nitrosoaromatic precursor as defined herein.

$R^3$ may be a moiety comprising nitrosobenzene, quinone dioxime or quinone oxime.

$R^1$ may be selected from $C_1$-$C_{24}$ alkyl, $C_3$-$C_{24}$ acyl. $R^1$ may be selected from $C_1$-$C_{24}$ alkyl, $C_3$-$C_{24}$ acyl and $R^2$ may be $OR^1$. X may be O. Y may be O or —$NH_x$ (where x=1). Y may be O. X and Y may be O. $R^1$ may be selected from $C_1$-$C_4$ alkyl, X may be O and $R^2$ may be $OR^1$. $R^1$ may be selected from $C_1$-$C_4$ alkyl, X may be O, Y may be O and $R^2$ may be $OR^1$. $R^1$ may be selected from $C_1$-$C_4$ alkyl, X may be O, Y may be —$NH_x$ (where x=1) and $R^2$ may be $OR^1$. $R^1$ may be selected from $C_1$-$C_4$ alkyl, X may be O, Y may be O, n may be 3, $R^2$ may be $OR^1$ and $R^3$ may be a moiety comprising nitrosobenzene. $R^1$ may be selected from $C_1$-$C_4$ alkyl, X may be O, Y may be O, n may be 3, $R^2$ may be $OR^1$, $R^3$ may be a moiety comprising nitrosobenzene, q may be 0, and m may be ≥2. $R^1$ may be selected from $C_1$-$C_4$ alkyl, X may be O, Y may be O, n may be 3, $R^2$ may be $OR^1$, $R^3$ may be a moiety comprising nitrosobenzene, q may be 0, m may be ≥2, and $R^4$ may be vinyl or ester.

Specific examples of compounds utilised in the method of the present invention may include the following:

-continued

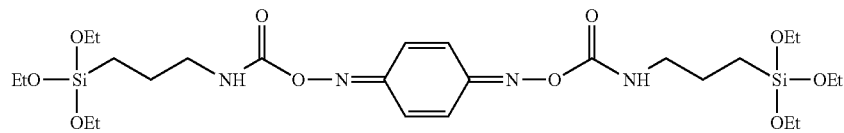

(D)

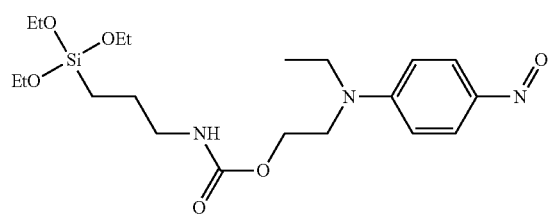

(E)

It will be appreciated that the compounds utilised in the method of the present invention may be formulated as part of a composition.

The so-described compounds and formulations may result in a number of advantages. For example, a one-part adhesive system may be formulated. Such systems are readily applied to substrates in a single step using convenient and conventional techniques, for example spraying or dipping. Compounds and formulations as so provided may have reduced toxicity as compared to conventional dinitrosobenzene formulations. Compounds and formulations as so provided can also achieve excellent bond strengths. In addition, cured compositions of the present invention exhibit hot water and solvent resistance.

Accordingly, the method of the present invention for bonding a polymer to a hydroxylated surface may comprise applying a composition (according to the present invention) to at least one of the polymer or surface, and mating the polymer and surface so as to form a bond, wherein the composition comprises:
(i) at least one compound comprising;
  a) at least one alkoxy silane moiety; and
  b) at least one moiety selected from an aromatic nitroso or an aromatic nitroso precursor and combinations thereof; and
(ii) a suitable carrier vehicle for the compound.

It will be appreciated that any suitable carrier vehicle may be utilised. It is desirable that the carrier vehicle should be environmentally friendly. Such compositions may find utility in bonding a substrate such as a glass substrate to a natural or synthetic rubber. The synthetic rubber may be a nitrile butadiene rubber. The synthetic rubber may be a hydrogenated nitrile butadiene rubber ("HNBR").

The compound comprising the at least one alkoxy silane moiety and the at least one moiety selected from an aromatic nitroso or an aromatic nitroso precursor (also known as a nitrososilane) may be present in an amount of 1 to 20% w/w of the total composition. Suitably, the nitrososilane may be present in an amount of 1 to 15% w/w, for example 4 to 12% w/w. The nitrososilane may be present in 6% w/w of the total composition.

Compositions utilised in the method of the present invention may find utility in any application where it is desirable to form an aromatic nitroso moiety in-situ. Similarly, compositions of the present invention may find utility in any application where it is desirable to form an aromatic dinitroso moiety in-situ. It will be appreciated that within these compositions the compound can react in-situ to form a nitrosobenzene moiety. It is also contemplated that the compound can react in-situ to form a dinitrosobenzene moiety. For example, for particularly good bonding it may be desirable for the compound to react in-situ to form apara-nitrosophenol moiety.

Compositions utilised in the method of the present invention may be one-part compositions. Compositions of the present invention may be two-part compositions.

Combinations of silanes (i.e. nitrososilanes and other silanes) may be employed in a composition utilised in the method of the present invention. For example, one or more silanes may be included within compositions utilised in method of the present invention. These silanes are generally of the formula:

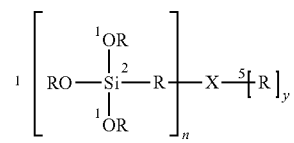

where:
n is either 1 or 2;
y=(2-n)
each $R^1$ can be selected from $C_1$-$C_{24}$ alkyl or $C_2$-$C_{24}$ acyl;
each $R^2$ can be selected from $C_1$-$C_{30}$ aliphatic groups, substituted $C_6$-$C_{30}$ aromatic groups, or unsubstituted $C_6$-$C_{30}$ aromatic groups;
$R^5$ can be selected from hydrogen, $C_1$-$C_{10}$ alkylene, $C_1$-$C_{10}$ alkylene substituted with one or more amino groups, $C_2$-$C_{10}$ alkenylene substituted with one or more amino groups, $C_6$-$C_{10}$ arylene, or $C_7$-$C_{20}$ alkylarlyene;
X—$R^5$ is optional and X is either:

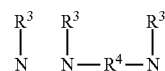

where each $R^3$ can be selected from hydrogen, $C_1$-$C_{30}$ aliphatic groups, or $C_6$-$C_{30}$ aromatic groups; and
$R^4$ can be selected from $C_1$-$C_{30}$ aliphatic groups, or $C_6$-$C_{30}$ aromatic groups; and
wherein when n=1, at least one of the $R^3$ and the $R^5$ is not hydrogen.

In one embodiment, X—$R^5$ is present. In this embodiment $R^1$ can be selected from $C_1$-$C_{24}$ alkyl, $R^2$ can be selected from $C_1$-$C_{30}$ aliphatic groups, X can be N—$R^3$ and $R^5$ can be selected from hydrogen or $C_1$-$C_{10}$ alkylene. As will be appreciated, when X—R$^5$ is absent the silane may be of the general formula (where R$_1$ and R$_2$ are as defined above):

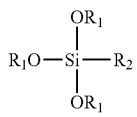

Preferred silanes include bis-silyl silanes such as those having two trisubstituted silyl groups. The substituents may be individually chosen from C$_1$-C$_{20}$ alkoxy, C$_6$-C$_{30}$ aryloxy and C$_2$-C$_{30}$ aryloxy. Suitable bis-silyl silanes for use within the present invention include:

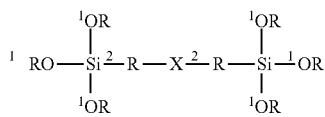

where:
each R$^1$ can be selected from C$_1$-C$_{24}$ alkyl or C$_2$-C$_{24}$ acyl;
each R$^2$ can be selected from C$_1$-C$_{20}$ aliphatic groups or C$_6$-C$_{30}$ aromatic groups;
X is optional and is either:

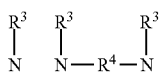

where each R$^3$ can be selected from hydrogen, C$_1$-C$_{20}$ aliphatic groups, or C$_6$-C$_{30}$ aromatic groups; and
R$^4$ can be selected from C$_1$-C$_{20}$ aliphatic groups or C$_6$-C$_{30}$ aromatic groups.

In one embodiment, X is present. R$^1$ can be selected from C$_1$-C$_{24}$ alkyl, R$^2$ can be selected from C$_1$-C$_{30}$ aliphatic groups, and X can be N—R$^3$. As will be appreciated, when X is absent the bis-silane may be of the general formula (where R$^1$ and R$^2$ are as defined above):

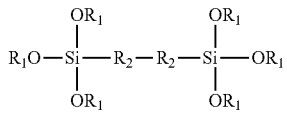

Examples of some bis-silyl aminosilanes formulated in compositions for use in the method of the present invention include: bis-(trimethoxysilylpropyl)amine, bis-(triethoxysilylpropyl)amine, bis-(triethoxysilylpropyl) ethylene diamine, N-[2-(vinylbenzylamino)ethyl]-3-aminopropyltrimethoxy silane, and aminoethyl-aminopropyltrimethoxy silane.

Such silanes (as described in the preceding paragraphs) may be included in the range of about 1:3 to about 3:1 (stoichiometrically) relative to the aromatic nitrososilane (or the aromatic nitrosoprecursor silane). Mixing of the aromatic nitrososilane and/or the aromatic nitrosoprecursor silane and the silanes described by the structural formulae in the preceding paragraphs may result in excellent rubber-to-glass bonding. In particular, the inclusion of the amino bis(propyltrimethoxysilane) in addition to the aromatic nitroso silane and/or the aromatic nitroso precursor silane may enhance rubber to glass bond strength significantly.

The silane may be present in an amount of 1 to 10% w/w of the total composition. Suitably, the silane may be present in an amount of 1 to 5% w/w, for example 1 to 3% w/w. The silane may be present in 3% w/w of the total composition.

Generally, the final solution applied to the target substrate may vary in the total silane concentration and ratio (silane to nitrososilane) over a wide range and still provide beneficial results. The final solution should contain a total silane concentration of at least approximately 0.1% by volume, i.e., the concentration of the combination of silanes and nitrososilanes in the final solution. Solutions having a total silane concentration of between about 0.1% and about 10% by volume generally provide strong bonding without waste of valuable silanes.

Excellent adhesion between elastomeric materials, such as rubber compositions, and surfaces comprising hydroxyl groups (e.g., glass and zeolites), with minimal waste of silane solution may be realized through the use of the compositions as so described.

For example, a first substrate may be constructed from a natural or synthetic rubber to be bonded to another substrate comprising surface hydroxyl groups. The second substrate comprising surface hydroxyl groups may be a glass substrate. Generally, the alkoxy silane moiety of the compound will anchor to a surface with hydroxyl groups. The moiety selected from an aromatic nitroso or an aromatic nitroso precursor will generally become anchored to the rubber. Accordingly, each end of the molecule is functionalised and assists in bonding the materials together with a strong and durable bond.

Thus, a glass substrate coated with an adhesive composition as so described may be adhered to a polymer such as an elastomeric material, for example a rubber composition, by applying the elastomer material in an uncured state onto the glass coated with the adhesive composition and curing the elastomeric material thereon to bond it to the glass. In the case of a rubber polymeric material the uncured rubber may be vulcanized in-situ to cure the rubber, resulting in further bonding of the rubber to the glass.

Such bonding to glass is achieved through the nitroso groups which are capable of reacting with polymers, in particular a polymer with alkene/allylic functionality within the polymer chain. For example, a polymer with diene or allylic functionality. Suitably, the polymer may comprise allylic functionality.

Alternatively, suitable polymers are those capable of reacting with nitroso groups so as to provide cross-links therebetween. Such a reaction produces a variety of cross-links for example between the nitroso group and a rubber material. The materials utilised in the method of the present invention are thought to reduce free nitroso groups as the nitroso group is within a molecular structure. In the reaction of the aromatic nitroso silane and/or the aromatic nitroso precursor silane and a glass substrate, the nitroso may react with alkene/allylic functionality within the natural rubber while the silane forms the bond with the glass.

In a further aspect the invention extends to a compound of the following general structure:

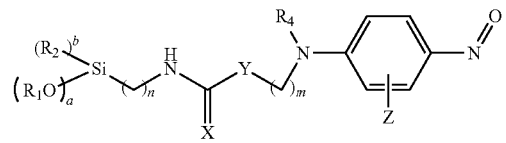

where 'a' can be 1-3 and 'b' can be 0-2; wherein a+b=3 and at least one alkoxy group is present;

$R^1$ can be selected from H, $C_1$-$C_{24}$ alkyl, $C_3$-$C_{24}$ acyl, preferably from $C_1$-$C_4$ alkyl and where when a≥1 at least one $R^1$ is not hydrogen;

$R^2$ can be selected from $C_1$-$C_{24}$ alkyl and $C_3$-$C_{24}$ acyl, preferably from $C_1$-$C_4$ alkyl;

m and n can be the same or different and can be 1-10;

X can be O or S;

Y can be —O, —S, or —$NH_x$ (where x=1 or 2);

$R_4$ can be $C_1$ to $C_{10}$; and

Z indicates that the rings of the above structures can optionally be mono-, di-, tri- or tetrasubstituted with the group consisting of $C_1$-$C_{20}$ alkyl, $C_3$-$C_{20}$ cycloalkyl, $C_1$-$C_{20}$ alkoxy, $C_3$-$C_{20}$ aralkyl, $C_3$-$C_{20}$ alkaryl, $C_5$-$C_{20}$ arylamine, $C_5$-$C_{20}$ arylnitroso, amino, hydroxy, halogen and combinations thereof, and further where the substituents can either be the same or different on each carbon atom of the ring. Such substitutions may be possible provided there is no interference with effective bonding or curing of a bonding composition comprising the compound.

$R^1$ may be selected from $C_1$-$C_{24}$ alkyl, $C_3$-$C_{24}$ acyl. $R^1$ may be selected from $C_1$-$C_{24}$ alkyl, $C_3$-$C_{24}$ acyl and 'a' may be 3. X may be O. Y may be O or —$NH_x$ (where x=1). Y may be O. X and Y may be O. n may be $C_2$-$C_5$ alkyl. m may be $C_2$-$C_5$ alkyl. $R^1$ may be selected from $C_1$-$C_4$ alkyl, X may be O and 'a' is 3. $R^1$ may be selected from $C_1$-$C_4$ alkyl, X may be O, Y may be O and 'a' may be 3. $R^1$ may be selected from $C_1$-$C_4$ alkyl, X may be O, Y may be —$NH_x$ (where x=1) and 'a' may be 3. $R^1$ may be selected from $C_1$-$C_4$ alkyl, X may be O, 'a' may be 3 and $R^4$ may be $C_1$ to $C_{10}$.

The compound may be:

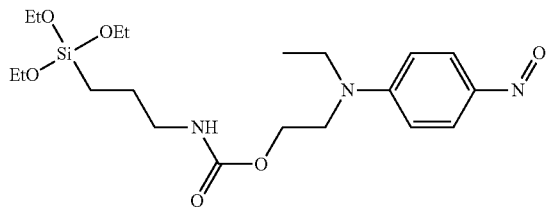 [SMILES: CCO[Si](CCCNC(=O)OCCN(CC)c1ccc(N=O)cc1)(OCC)OCC]

In a further aspect, the present invention extends to an adhesive composition comprising a compound of the present invention. The composition may further comprise a suitable carrier vehicle for the compound. The composition may additionally comprise a silane (as described above), such as an aminosilane.

The composition of the present invention may find utility in bonding polymeric substrates, for example, elastomeric substrates to non-elastomeric substrates. One example is rubber (natural or synthetic) to non-rubber substrates, for example in bonding glass to natural or synthetic rubber. The synthetic rubber may be a nitrile butadiene rubber. The synthetic rubber may be a HNBR.

The invention further extends to a cured residue between a hydroxylated surface and a polymeric substrate having diene and or allylic functionality within the polymer chain (such as an elastomer, for example a natural or synthetic rubber), the residue comprising a silane anchored to the hydroxylated surface and the cycloaddition reaction product of a nitroso group and a diene or allyl group of the polymeric substrate. The hydroxylated surface and the polymer substrate are not part of the residue.

For example, when the polymeric substrate comprises allylic functionality with the polymer chain (for example in a natural or synthetic rubber), the residue may be of the following general structure (wherein the hydroxylated surface and the polymer substrate are not part of the residue):

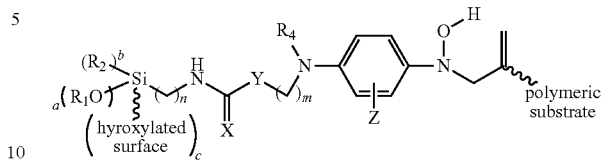

where 'a' can be 0-2, 'b' can be 0-2 and c can be 1 to 3, such that a+b+c=3;

$R^1$ can be selected from H, $C_1$-$C_{24}$ alkyl, $C_3$-$C_{24}$ acyl, preferably from $C_1$-$C_4$ alkyl and where when a≥1 at least one $R^1$ is not hydrogen; and $R^2$ can be selected from $C_1$-$C_{24}$ alkyl and $C_3$-$C_{24}$ acyl, preferably from $C_1$-$C_4$ alkyl;

m and n can be the same or different and can be 1-10;

X can be O or S;

Y can be —O, —S, or —$NH_x$ (where x=1 or 2);

$R_4$ can be $C_1$ to $C_{10}$; and

Z indicates that the rings of the above structures can optionally be mono-, di-, tri- or tetrasubstituted with $C_1$-$C_{20}$ alkyl, $C_3$-$C_{20}$ cycloalkyl, $C_1$-$C_{20}$ alkoxy, $C_7$-$C_{20}$ aralkyl, $C_7$-$C_{20}$ alkaryl, $C_5$-$C_{20}$ arylamine, $C_5$-$C_{20}$ arylnitroso, amino, hydroxy, halogen and combinations thereof, and further where the substituents can either be the same or different on each carbon atom of the ring. Such substitutions may be possible provided there is no interference with effective bonding or curing of a bonding composition comprising the compound.

In a further aspect, the invention extends to a cure product comprising a substrate and a composition according to the present invention. The invention further extends to an assembly comprising at least two substrates bonded together by an adhesive composition according to the present invention.

In yet a further aspect the present invention provides a process for bonding two substrates together comprising the steps of:
(i) applying a primer comprising a silicate, an aluminate, a germanate or combinations thereof to at least one substrate;
(ii) applying a compound comprising;
   a) at least one alkoxy silane moiety; and
   b) at least one moiety selected from an aromatic nitroso or an aromatic nitroso precursor and combinations thereof;
to at least one substrate, and
(iii) mating the first and second substrates so as to form a bond with the composition.

As used herein, the term "applying a primer comprising a silicate, an aluminate, a germanate or combinations thereof" refers to applying an amount of a silicate, an aluminate, a germanate or combinations thereof to a surface for subsequent application of a compound comprising at least one alkoxy silane moiety and at least one aromatic nitroso (precursor) moiety. For example, the primer comprising a silicate, an aluminate, a germanate or combinations thereof may be applied as a deposit, monolayer, thin film, layer, etc. Suitably, a primer comprising a silicate, an aluminate, a germanate or combinations thereof may be applied to the surface of a first substrate for the purpose of priming said first substrate for subsequent bonding to a second substrate. The primer may comprise a silicate, an aluminate or combinations thereof. The second substrate may be an elastomer, for example a natural or synthetic rubber. The synthetic rubber may be a nitrile butadiene rubber. The synthetic rubber may be HNBR.

The primer comprising a silicate, an aluminate, a germanate or combinations thereof may be applied to one substrate or both substrates. Advantageously, applying a primer comprising a silicate, an aluminate, a germanate or combinations thereof to substrates may result in improved cure strength, particularly in production and automated processes.

The primer comprising a silicate, an aluminate, a germanate or combinations thereof may be applied to the at least one substrate in a suitable carrier. For example, the carrier may be a solvent, a wetting agent or a dispersing medium.

The primer may comprise a component selected from the group comprising glass such as glass fibres, quartz, clays, talcs, zeolites, porcelains, ceramics, silicon substrates and combinations thereof. The primer may comprise a silicate.

The compound comprising at least one alkoxy silane moiety; and at least one moiety selected from an aromatic nitroso or an aromatic nitroso precursor and combinations thereof may comprise a compound according to any of the generic formulae or specific formulae as disclosed herein.

A first substrate may be a polymer. The polymer may comprise diene or allylic functionality within the polymer chain. For example, the polymer may be an elastomer, such as natural or synthetic rubber. The synthetic rubber may be a nitrile butadiene rubber. The synthetic rubber may be a hydrogenated nitrile butadiene rubber (HNBR). The primer may be applied to the polymeric substrate. The primer may be applied to the other substrates which do not have any or sufficient diene and or allylic functionality.

At least one of the substrates may be a natural or synthetic rubber. The process may further comprise the step of vulcanising or crosslinking the rubber. One desirable process involves vulcanisation of the rubber and bonding to the second substrate at the same time.

The inventive primers and compounds (and compositions) utilised in the method of the present invention may be used in a pre-applied format. As used herein, the term pre-applied indicates that the primer or compound or compositions of the present invention may be applied to a substrate such that it remains secured thereto, and the resulting pre-treated substrate is suitable for storage. The primer or compound of composition should retain its efficacy over time. The pre-treated substrate may be stored for subsequent bonding to a second substrate.

For example, this may involve pre-applying a primer comprising a silicate, an aluminate, a germanate or combinations thereof to a first substrate, such that it remains secured thereto. Advantageously, substrates can be primed in a pre-treatment process, optionally stored, and subsequently utilised in (automated) manufacturing processes.

Accordingly, the invention further provides for a substrate having a primer comprising a silicate, an aluminate, a germanate or combinations thereof applied thereto for the purpose of priming said substrate for subsequent bonding to a second substrate using a compound comprising at least one alkoxy silane moiety; and at least one moiety selected from an aromatic nitroso or an aromatic nitroso precursor and combinations thereof. At least one of the substrates may comprise a polymer comprising diene or allylic functionality within the polymer chain, for example, the polymer may be an elastomer, such as natural or synthetic rubber. The synthetic rubber may be a nitrile butadiene rubber. The synthetic rubber may be HNBR.

The invention further provides for a substrate having a compound comprising at least one alkoxy silane moiety; and at least one moiety selected from an aromatic nitroso or an aromatic nitroso precursor and combinations thereof pre-applied thereto for subsequent bonding to a second substrate. A first substrate may comprise a hydroxylated surface as defined herein. A second substrate may comprise a polymer. The polymer may comprise diene or allylic functionality within the polymer chain, for example, the polymer may be an elastomer, such as natural or synthetic rubber. The synthetic rubber may be a nitrile butadiene rubber. The synthetic rubber may be HNBR. Advantageously, substrates can be pre-treated and subsequently utilised in (automated) manufacturing processes.

The primer or compound or composition of the present invention may be pre-applied to the polymeric substrate (such as an elastomer, for example a natural or synthetic rubber), or the hydroxylated surface. The composition may be pre-applied to the hydroxylated surface.

The inventive methods, compounds and compositions of the present invention may find utility in the following non-limiting applications: manufacture of automotive timing belts, bonding to glass/glass fibre reinforced plastic and composite parts, manufacture of reinforced rubbers, tyre manufacture, conveyor belt manufacture and the manufacture of woven materials such as clothing, for example protective clothing.

It will be appreciated by a person skilled in the art that the compositions of the present invention may additionally comprises conventional additives such as fillers, pigments, stabilisers, and/or moisture scavengers, subject to said additives not interfering with effective curing of the compositions.

Where suitable, it will be appreciated that all optional and/or preferred features of one embodiment of the invention may be combined with optional and/or preferred features of another/other embodiment(s) of the invention.

DETAILED DESCRIPTION

The rubber compositions utilised in bonding according to the method of the present invention may further include known additives common to rubber compositions. These include reinforcing carbon blacks; inactive fillers such as calcium carbonates, chalks, talcs, or metal oxides; accelerator systems; vulcanization retarders; promoters such as zinc oxide or stearic acid; plasticizers such as aromatic, paraffinic, naphthenic and synthetic mineral oils; ageing, light-protecting ozone-protecting, fatigue, coloration, and processing auxiliaries; and sulfur. Commonly these additives may be present at a quantity of about 0.1 parts to about 80 parts per 100 parts by weight of the rubber composition.

Prior to application of the silane solution, the surface to be coated with the adhesive composition may be cleaned to allow better adhesion. For example, cleaning with solvent or alkaline material or cleaning with an abrasive agent. Application can then be conducted by a variety of methods, including dipping, spraying, brushing or wiping the solution onto the substrate. It has been suggested that for improving rubber adhesion the coating remain partially cross-linked prior to vulcanisation. For this reason, the coating is usually air dried at room temperature as heat drying can cause a higher degree of cross-linking that will result in poorer adhesion.

Compounds of the invention were made as set out below.

EXAMPLES

Compounds A, B, C, D and E (supra) were synthesised according to the following experimental procedures and as illustrated in the reaction schemes below.

Nitrosylation Reaction (1):

(infra) was carried out as outlined in J. J. D'Amico, C. C. Tung and L. A. Walker, *J. Am. Chem. Soc.*, 5957 (1959):

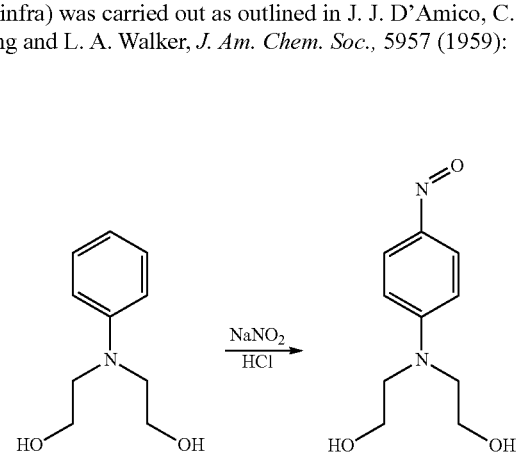

Reaction (2):

γ-Isocyantopropyltriethoxysilane (GE Bayer Silicones A-1310) (2.35 g, 9.5 mmol) was solvated in 10 mL of anhydrous THF in a 50 mL round bottom flask. The reaction flask was flushed with nitrogen and charged with N,N-bis-(2-hydroxyethyl)-4-nitroso-aniline (2 g, 9.5 mmol), followed by a catalytic quantity of dibutyltin dilaurate (1.5 µmol). The reaction was refluxed for an additional 2 hours under nitrogen. Consumption of the isocyanate (2275 cm$^{-1}$) was monitored using infrared spectroscopy. The solvents were removed under reduced pressure to give the product in a quantitative yield.

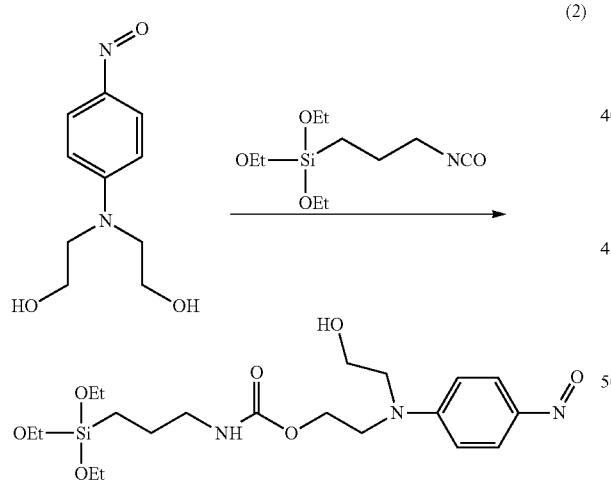

Reaction (3):

γ-Isocyantopropyltrimethoxysilane (ABCR GmbH) (1.5 g, 7.3 mmol) was solvated in 8 mL of anhydrous THF in a 50 mL round bottom flask. The reaction flask was flushed with nitrogen and charged with N,N-bis-(2-hydroxyethyl)-4-nitroso-aniline (1.53 g, 7.3 mmol), followed by a catalytic quantity of dibutyltin dilaurate (1 µmol). The reaction was refluxed for an additional 2 hours under nitrogen. Consumption of the isocyanate (2275 cm$^{-1}$) was monitored using infrared spectroscopy. The solvents were removed under reduced pressure to give the product in a quantitative yield.

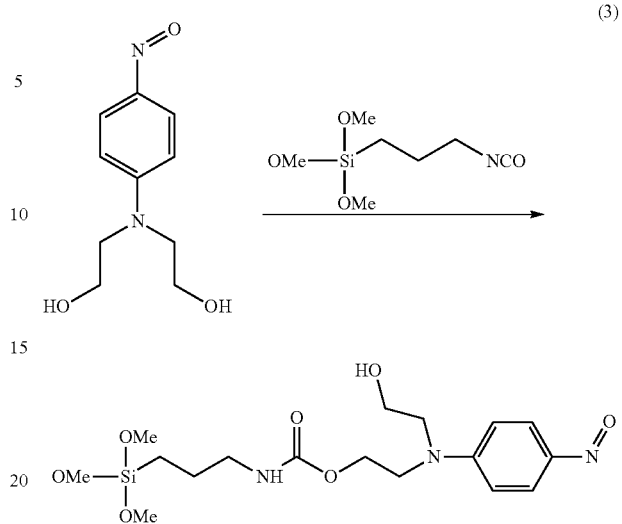

Reaction (4):

γ-Isocyantopropyltriethoxysilane (GE Bayer Silicones A-1310) (2.35 g, 9.5 mmol) was solvated in 10 mL of anhydrous THF in a 50 mL round bottom flask. The reaction flask was flushed with nitrogen and charged with N,N-bis-(2-hydroxyethyl)-4-nitroso-aniline (1 g, 4.75 mmol), followed by a catalytic quantity of dibutyltin dilaurate (1.5 µmol). The reaction was refluxed for an additional 5 hours under nitrogen. Consumption of the isocyanate (2275 cm$^{-1}$) was monitored using infrared spectroscopy. The solvents were removed under reduced pressure to give the product in a quantitative yield.

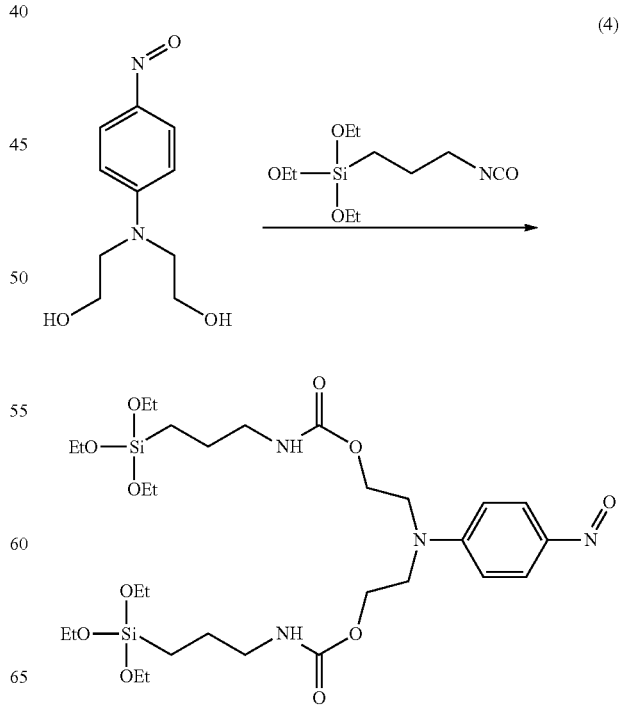

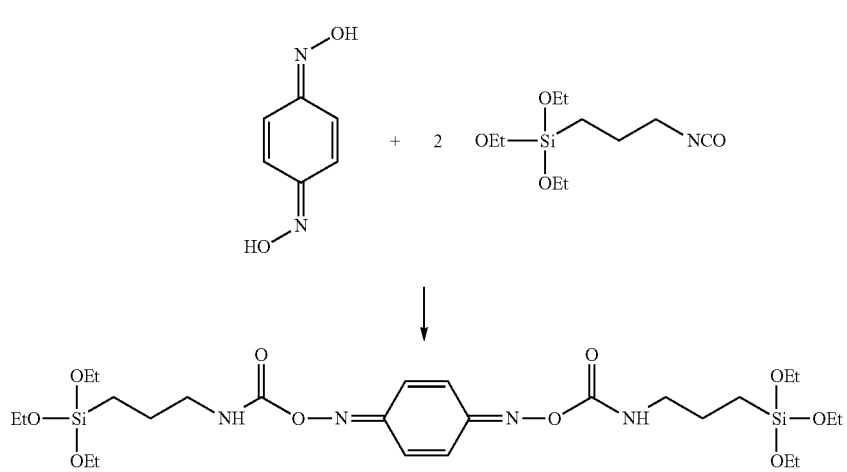

(5)

Reaction (5):

γ-Isocyantopropyltriethoxysilane (GE Bayer Silicones A-1310) (10.68 g, 43.18 mmol) was solvated in 30 mL of anhydrous THF in a 100 mL round bottom flask. The reaction flask was flushed with nitrogen and charged with p-benzoquinone dioxime (Sigma-Aldrich) (3 g, 21.72 mmol), followed by a catalytic quantity of dibutyltin dilaurate (1.5 μmol). The reaction was refluxed for an additional 5 hours under nitrogen. Consumption of the isocyanate (2275 cm$^{-1}$) was monitored using infrared spectroscopy. The solvents were removed under reduced pressure to give the product in a quantitative yield.

Reaction (6):

γ-Isocyantopropyltriethoxysilane (GE Bayer Silicones A-1310) (2.35 g, 9.5 mmol) was solvated in 10 mL of anhydrous THF in a 50 mL round bottom flask. The reaction flask was flushed with nitrogen and charged with 2-(N-ethylanilino)ethanol (0.78 g, 4.75 mmol), followed by a catalytic quantity of dibutyltin dilaurate (1.5 μmol). The reaction was refluxed for an additional 5 hours under nitrogen. Consumption of the isocyanate (2275 cm$^{-1}$) was monitored using infrared spectroscopy. The solvents were removed under reduced pressure to give the product in a quantitative yield.

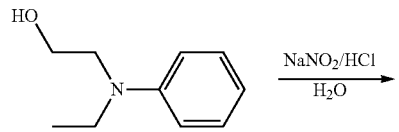

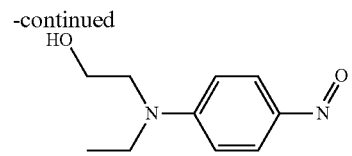

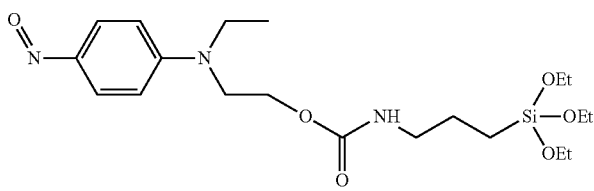

Formulations comprising the compounds of the invention were prepared as set out below. Bis(trimethoxysilylpropyl) amine is commercially available from Sigma Aldrich and is of the formula:

| Compositions Used in Natural Rubber Bonding | |
|---|---|
| (E) | |

| Ingredient | Level (Weight %) |
|---|---|
| Compound E | 6.4 |
| Bis(triethoxysilylpropyl) amine | 1.3 |
| Superchlon HE1200 | 8.9 |
| Isopropanol | 8.4 |
| MEK | 29.0 |
| Xylene | 46.0 |

Natural Rubber Composition—Available From Merl Ltd. (Merl Sulfur Cured NR60)

Tests were carried out using natural rubber of the following composition:

| Ingredient | Parts by weight |
|---|---|
| Natural Rubber[a] | 100 |
| Zinc Oxide | 3.5 |
| Stearic Acid | 2 |
| Carbon Black[b] | 40 |
| Naphthenic Oil (low viscosity)[c] | 5 |
| 1,2-Dihydro-2,2,4-Trimethylquinoline[d] | 2 |
| N-(1,3-dimethylbutyl)-N'-phenyl-p-phenylenediamine[e] | 1 |
| Hydrocarbon Waxes[f] | 2 |
| CBS[g] | 0.7 |
| Sulphur | 2.5 |

[a]NR SMR CV 60;
[b]SRF N762 black;
[c]Oil Strukthene 410;
[d]Flectol H;
[e]Santoflex 13 (HPPD);
[f]Sunproof Improved Wax;
[g]Vulcanisation accelerator, N-Cyclohexyl-2-benzothiazole.

Testing

To assess the efficacy of the adhesive systems of the present invention in bonding rubbers to a number of substrates, a series of tests were performed according to the ASTM 429-B standard adjusted to a 45° angle. The substrates (2.54 cm (1 inch) wide, 10.16 cm (4 inch) long panels or coupons) were coated with the adhesive and adhered to natural rubber in a vulcanisation process. The natural rubber compositions were sulfur-cured compositions as set out in the Formulation table supra.

Typically the substrates were wiped with a dry cloth. The substrates were also subjected to grit-blasting, followed by a second wiping with a dry cloth. Before application of the adhesive, 2.54 cm (1 inch) of length and 2.54 cm wide (1 inch) on both ends of the substrate/coupon was masked to prevent that region.

Typically the substrates were wiped with a dry cloth. The substrates were also subjected to grit-blasting, followed by a second wiping with a dry cloth. Before application of the adhesive, 2.54 cm (1 inch) of length and 2.54 cm wide (1 inch) on both ends of the substrate/coupon was masked to prevent that region being available for bonding to the rubber, leaving a central area of 2.54 cm (1 inch) in width and 5.08 cm (2 inches) in length available to bond to the rubber.

In the bonding operation of the present invention, the compositions are applied to the substrates by either a dipping, spraying or brush method to ensure an even coverage, preferably after the substrate has been cleaned.

Drying may be carried out under ambient room temperature conditions. Solvent evaporation rate can be increased by heat, forced air or both.

A layer of uncured rubber was then placed on each coupon and cured in a standard hydraulic vulcanisation press for a period of time specified by the rubber's cure profile. In the case of the natural rubber used in the bonding process in the present invention, the rubber was cured for 20 minutes at 150° C. under a pressure of 20-30 Tonnes, to ensure intimate contact of the surfaces being bonded and the adhesive.

After curing the bonded samples were aged for 24 hours at room temperature before being subjected to testing and the tear pattern noted. Each sample was tested by the 45° angle modified ASTM 429-B standard using Instron equipment (Instron tester, Model No. 5500R) at a load rate of 50 mm per minute until separation is complete.

RESULTS

A number of different substrates were tested as set out below in Table 1.

TABLE 1

| Entry | Substrate | Grit-blasted (N/mm) | Non Grit-blasted (N/mm) |
|---|---|---|---|
| 1 | Glass lap (Control)[a] | Strong Bond, resulting in 100% rubber failure | Strong Bond, resulting in 100% rubber failure |
| 2 | Polypropylene[b] | No bond | No bond |
| 3 | FR4 Epoxy Glass-epoxy resin reinforced with woven fibre glass mat[c] | 14.690 | 17.804 |
| 4 | Polypropylene 30% reinforced with Glass fibre[d] | 8.686* | No Bond |
| 5 | Nylon 66 containing 20% Talc[b] | 11.467 | No Bond |
| 6 | Polypropylene containing 20% Talc[d] | 10.059* | No Bond |

*Significant substrate deformation observed.
[a]available from Ideal Glass Ltd;
[b]available from William Cox Ltd. (Also Goodfellow);
[c]GSPK Circuits Ltd.
[d]available from Rocholl GmbH.

Entry 1, the glass slide substrate, represents the control reaction. Very strong bonds were observed, typically resulting in rubber failure prior to bond failure. Rubber coverage is the percentage of rubber remaining on the bonded substrate after peel testing. 100% Rubber failure means that the rubber completely failed with no portion of the rubber peeling away from the surface of the substrate (and equates to 100% rubber failure). Generally, it is desirable that the rubber substrate fails before the substrate to rubber bond fails. Entry 2, i.e. a polypropylene substrate, is the second control reaction. No bond is formed between the rubber composition and this substrate.

Entries 1 and 3 in Table 1 exhibit good bond strengths to rubber irrespective of whether the substrate was grit-blasted prior to cure. However, entries 4 to 6 show strong dependence on whether the substrate has been grit-blasted. Grit-blasted substrates exhibit good bond strengths. However, absent a pre-treatment grit-blasting step, the same substrates failed to show any bonding to the rubber substrate. One possible suggestion for this observation is that grit-blasting reveals nascent hydroxyl groups in the substrates, thereby greatly enhancing the ability of the adhesive to bond the substrate and rubber together.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

The invention claimed is:

1. A process for bonding two substrates together comprising the steps of:
   (i) applying a primer comprising a silicate, an aluminate, a germinate or combinations thereof to at least one substrate;
   (ii) applying a compound comprising;
      a) at least one alkoxy silane moiety; and
      b) at least one moiety selected from an aromatic nitroso or an aromatic nitroso precursor and combinations thereof;
   to at least one substrate, and
   (iii) mating the first and second substrates so as to form a bond with the composition.

2. A process according to claim 1, further comprising the step of heating at least one of the first or second substrates subsequent to bringing the substrates together.

3. A process according to claim 1 wherein the least one moiety selected from an aromatic nitroso or an aromatic nitroso precursor is a nitrosobenzene or a nitrosobenzene precursor.

4. A process according to claim 1 wherein said alkoxy silane moiety is of the structure:

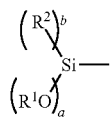

wherein 'a' can be 1-3 and 'b' can be 0-2, wherein a+b=3 and at least one alkoxy group is present;

$R^1$ can be selected from the group consisting of H, $C_1$-$C_{24}$ alkyl, $C_3$-$C_{24}$ acyl, wherein when a ≥1 at least one $R^1$ is not hydrogen; and $R^2$ can be selected from $C_1$-$C_{24}$ alkyl and $C_3$-$C_{24}$ acyl.

5. A process according to claim 1 wherein the compound is of the general structure:

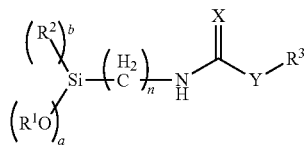

wherein n can be 1-10;

'a' can be 1-3 and 'b' can be 0-2; wherein a+b=3 and at least one alkoxy group is present;

$R^1$ can be selected from the group consisting of H, $C_1$-$C_{24}$ alkyl, $C_3$-$C_{24}$ acyl, and wherein when a ≥1 at least one $R^1$ is not hydrogen;

$R^2$ can be selected from $C_1$-$C_{24}$ alkyl and $C_3$-$C_{24}$ acyl;

X can be O or S;

Y can be —O, —S, or —N($R^3$); and $R^3$ can be a moiety comprising nitrosoaromatic, or a nitrosoaromatic precursor.

6. A process according to claim 5 wherein $R^3$ is a moiety comprising nitrosobenzene, quinone dioxime or quinone oxime.

7. A process according to claim 5 wherein $R^3$ is selected from the group comprising (showing linkage through Y):

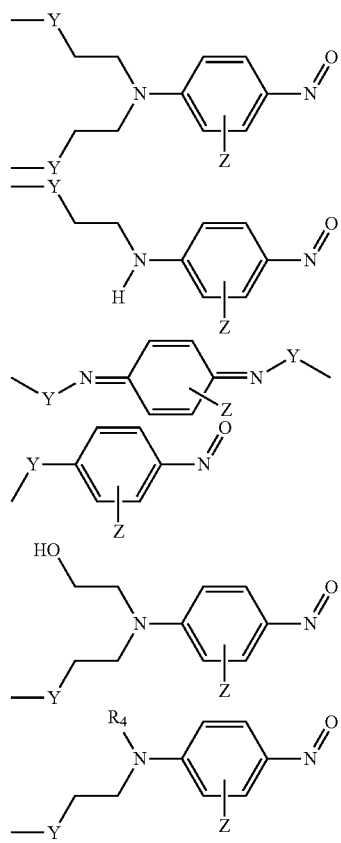

wherein $R_4$ can be $C_1$ to $C_{10}$; and

Z indicates that the rings of the above structures can optionally be mono-, di-, tri- or tetrasubstituted with the group consisting of $C_1$-$C_{20}$ alkyl, $C_3$-$C_{20}$ cycloalkyl, $C_1$-$C_{20}$ alkoxy, $C_7$-$C_{20}$ aralkyl, $C_7$-$C_{20}$ alkaryl, $C_5$-$C_{20}$ arylamine, $C_5$-$C_{20}$ arylnitroso, amino, hydroxy, halogen and combinations thereof, and further wherein the substituents can either be the same or different on each carbon atom of the ring.

8. An assembly comprising at least two substrates bound together by a process according to claim 1.

9. An article of manufacture prepared utilising the process according to claim 1.

10. An article according to claim 9, wherein the article is selected from the group comprising automotive timing belts, glass fibre reinforced plastics and composite materials, reinforced rubbers, tires, conveyor belts and woven articles.

* * * * *